United States Patent
Wu et al.

(10) Patent No.: US 7,373,277 B1
(45) Date of Patent: May 13, 2008

(54) METHODS AND SYSTEMS FOR DETECTION OF SELECTED DEFECTS PARTICULARLY IN RELATIVELY NOISY INSPECTION DATA

(75) Inventors: Sean Wu, Fremont, CA (US); Haiguang Chen, Millbrae, CA (US); Michael D. Kirk, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 19 days.

(21) Appl. No.: 10/858,420

(22) Filed: Jun. 1, 2004

Related U.S. Application Data

(60) Provisional application No. 60/551,618, filed on Mar. 9, 2004.

(51) Int. Cl.
*G06F 11/30* (2006.01)
(52) U.S. Cl. .................................... 702/185
(58) Field of Classification Search ................ 702/185
See application file for complete search history.

(56) References Cited

U.S. PATENT DOCUMENTS

| | | | |
|---|---|---|---|
| 3,069,654 A | 12/1962 | Hough | |
| 5,418,892 A | 5/1995 | Aghajan et al. | |
| 5,430,810 A | 7/1995 | Saeki | |
| 5,471,066 A * | 11/1995 | Hagiwara | 250/559.48 |
| 6,229,928 B1 * | 5/2001 | Matsuzawa | 382/255 |
| 6,268,935 B1 | 7/2001 | Kingetsu et al. | |
| 6,292,583 B1 | 9/2001 | Maruo | |
| 6,324,299 B1 | 11/2001 | Sarachik et al. | |
| 6,330,354 B1 | 12/2001 | Companion et al. | |
| 6,408,105 B1 | 6/2002 | Maruo | |
| 6,544,805 B2 | 4/2003 | Holcman et al. | |
| 6,574,366 B1 | 6/2003 | Fan | |
| 6,665,449 B1 | 12/2003 | He et al. | |
| 6,810,139 B2 * | 10/2004 | Smilansky et al. | 382/149 |
| 2002/0181756 A1 | 12/2002 | Shibuya et al. | |
| 2004/0064269 A1 * | 4/2004 | Shibuya et al. | 702/40 |

* cited by examiner

*Primary Examiner*—John Barlow
*Assistant Examiner*—Aditya S. Bhat
(74) *Attorney, Agent, or Firm*—Baker & McKenzie LLP

(57) ABSTRACT

Various methods and systems for detection of selected defects particularly in relatively noisy inspection data are provided. One method includes applying a spatial filter algorithm to raw inspection data acquired across an area on a substrate to determine a first portion of the raw inspection data that has a higher probability of being a selected type of defect than a second portion of the raw inspection data. The selected type of defect includes a non-point defect. The method also includes generating a raw two-dimensional map illustrating the first portion of the raw inspection data. In addition, the method includes searching the raw two-dimensional map for an event that has spatial characteristics that approximately match spatial characteristics of the selected type of defect. The method further includes determining if the event corresponds to a defect having the selected type.

25 Claims, 5 Drawing Sheets

METHODS AND SYSTEMS FOR DETECTION OF SELECTED DEFECTS PARTICULARLY IN RELATIVELY NOISY INSPECTION DATA

PRIORITY CLAIM

This application claims priority to U.S. Provisional Application No. 60/551,618 entitled "Methods and Systems for Detection of Selected Defects Particularly in Relatively Noisy Inspection Data," filed Mar. 9, 2004, which is incorporated by reference as if fully set forth herein.

BACKGROUND OF THE INVENTION

1. Field of the Invention

The present invention generally relates to methods and systems for detection of defects particularly in relatively noisy inspection data. Certain embodiments relate to a computer-implemented method for detecting one or more selected types of defects in relatively noisy inspection data based on spatial characteristics of the defects.

2. Description of the Related Art

Fabricating semiconductor devices such as logic and memory devices typically includes processing a substrate such as a semiconductor wafer using a number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

As the dimensions of advanced semiconductor devices continue to shrink, the presence of defects in the semiconductor devices increasingly limits the successful fabrication, or yield, of the semiconductor devices. For example, a scratch formed on a wafer during chemical-mechanical polishing may cause an open circuit or a short circuit in, or complete failure of, one or more semiconductor devices formed in subsequent processing. Because fabrication of a semiconductor device includes many complex process steps, the adverse effects of defects on total yield may increase exponentially if a defect formed on a wafer in one manufacturing process step causes additional defects to be formed on the wafer in subsequent manufacturing process steps.

Accordingly, defect detection or "inspection" of semiconductor wafers is and will continue to be of significant importance in semiconductor development and manufacturing. Furthermore, the ability of inspection tools or systems to detect a range of defect types over a range of sensitivities will determine how well defects can be detected and, therefore, how well semiconductor fabrication processes can be monitored and controlled. Consequently, significant efforts have been and will continue to be made to increase the sensitivity of inspection systems by improving parameters of the systems such as resolution. There have also been significant efforts in improving the processing of inspection data to increase the accuracy with which defects can be detected.

However, most inspection data processing involves two steps: defect detection and then classification. For instance, on many commercially available inspection systems, defects are found by detecting point defects via signal thresholding on individual data points in simple one-dimensional scans. Individual point defects may then be displayed on a point defect map or organized into another format. The point defect map is then post-processed to recognize if several of the points fall roughly into a two-dimensional shape, at which point that collection of points is labeled or classified as a specific defect instead of as individual particle defects.

There are, however, several disadvantages to the above methods of inspection data processing for detecting the presence of particular types of defects. In particular, these methods can be relatively inaccurate when detecting defects in relatively noisy inspection data. For example, as described above, simple one-dimensional scans only generate raw signals at individual points on the substrate, and every encounter with a two-dimensional surface anomaly is treated as a disconnected collection of point defects. Therefore, signal thresholding yields a defect map determined solely by signal strength at the individual points. Consequently, portions of faint two-dimensional defects may be lost to background noise due to failure of some of its associated point defect signals to exceed the threshold. As a result, the above-described methods for detecting defects may be substantially inaccurate when detecting defects in noisy inspection data since many defects may not be detected at all. In addition, the above-described methods for detecting defects may be substantially inaccurate in detecting the types of defects that are present on a substrate since portions of defects may not be detected thereby increasing the probability of misclassification of defects.

Accordingly, it may be advantageous to develop methods and systems for detecting defects on a substrate that are substantially accurate for detecting a range of defect types having a range of sensitivities, particularly in relatively noisy inspection data.

SUMMARY OF THE INVENTION

An embodiment of the invention relates to a computer-implemented method for detecting defects on a substrate. The method includes applying a spatial filter algorithm to raw inspection data acquired across an area on the substrate to determine a first portion of the raw inspection data that has a higher probability of being a selected type of defect than a second portion of the raw inspection data. The selected type of defect includes a non-point defect. In other words, the selected type of defect has some lateral extent in two dimensions.

The raw inspection data may contain a significant amount of noise. For example, the raw inspection data may have a relatively low signal-to-noise ratio. In some embodiments, the raw inspection data includes one or more raw scan images. In one embodiment, the area on the substrate, across which the raw inspection data has been acquired, equals approximately an area of a surface of the substrate. The raw inspection data may include data acquired by optical inspection of the substrate. The substrate may include a wafer or a reticle. In another embodiment, the substrate may include a patterned wafer.

The method also includes generating a raw two-dimensional map illustrating the first portion of the raw inspection data. In some embodiments, applying the spatial filter algorithm to the raw inspection data includes extracting the first portion of the raw inspection data. In such an embodiment, the raw two-dimensional map may illustrate only the first portion of the raw inspection data. In another embodiment, the method may include accentuating the first portion of the raw inspection data. In this embodiment, the raw two-dimensional map illustrates the accentuated first portion of the raw inspection data. This raw two-dimensional map may or may not also illustrate the second portion of the raw inspection data.

In addition, the method includes searching the raw two-dimensional map for an event that has spatial characteristics that approximately match spatial characteristics of the selected type of defect. In one embodiment, the selected type of defect includes a scratch. In this and other embodiments, the spatial characteristics of the selected type of defect may be substantially linear. In one such embodiment, searching the raw two-dimensional map includes applying a Hough transform to the raw two-dimensional map. The method further includes determining if the event corresponds to a defect having the selected type. In some embodiments, determining if the event corresponds to a defect includes applying a thresholding algorithm to the event.

In some embodiments, the method may include generating a processed two-dimensional map illustrating only the defect having the selected type. In an additional embodiment, the method may include substantially simultaneously searching the raw two-dimensional map for one or more events that have spatial characteristics that approximately match spatial characteristics of more than one selected type of defect. Such a method may also include determining if the one or more events correspond to defects having one of the more than one selected type. Each of the above described embodiments may also include any additional steps described herein.

Another embodiment relates to a carrier medium that includes program instructions executable on a processor. The program instructions are executable for applying a spatial filter algorithm to raw inspection data acquired across an area on a substrate to determine a first portion of the raw inspection data that has a higher probability of being a selected type of defect than a second portion of the raw inspection data. The raw inspection data may contain a significant amount of noise. For example, in one embodiment, the raw inspection data may have a relatively low signal-to-noise ratio. The selected type of defect includes a non-point defect.

The program instructions are also executable for generating a raw two-dimensional map illustrating the first portion of the raw inspection data. In one embodiment, applying the spatial filter algorithm to the raw inspection data may include extracting the first portion of the raw inspection data. In such an embodiment, the raw two-dimensional map may illustrate only the first portion of the raw inspection data. In another embodiment, the program instructions may be further executable for accentuating the first portion of the raw inspection data. In this embodiment, the raw two-dimensional map may illustrate the accentuated first portion of the raw inspection data. This raw two-dimensional map may or may not also illustrate the second portion of the raw inspection data.

In addition, the program instructions are executable for searching the raw two-dimensional map for an event that has spatial characteristics that approximately match spatial characteristics of a selected type of defect. The selected type of the defect includes a scratch in one embodiment. Therefore, in this and in other, embodiments, the spatial characteristics of the selected type of defect may be substantially linear. In one such embodiment, searching the raw two-dimensional map may include applying a Hough transform to the raw two-dimensional map. The program instructions are further executable for determining if the event corresponds to a defect having the selected type. In some embodiments, determining if the event corresponds to a defect may include applying a thresholding algorithm to the event. Each of the embodiments of the carrier medium described above may be further configured as described herein.

An additional embodiment relates to a system that is configured to detect defects on a substrate. The system includes a processor and a carrier medium. The carrier medium includes program instructions executable on the processor. The program instructions are executable for applying a spatial filter algorithm to raw inspection data acquired across an area on the substrate to determine a first portion of the raw inspection data that has a higher probability of being a selected type of defect than a second portion of the raw inspection data. The selected type of defect includes a non-point defect. The program instructions are also executable for generating a raw two-dimensional map illustrating the first portion of the raw inspection data. In addition, the program instructions are executable for searching the raw two-dimensional map for an event that has spatial characteristics that approximately match spatial characteristics of the selected type of defect. The program instructions are further executable for determining if the event corresponds to a defect having the selected type. In some embodiments, the system may also include an inspection module coupled to the processor. The inspection module may be configured to generate the raw inspection data. The embodiments of the system described above may be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
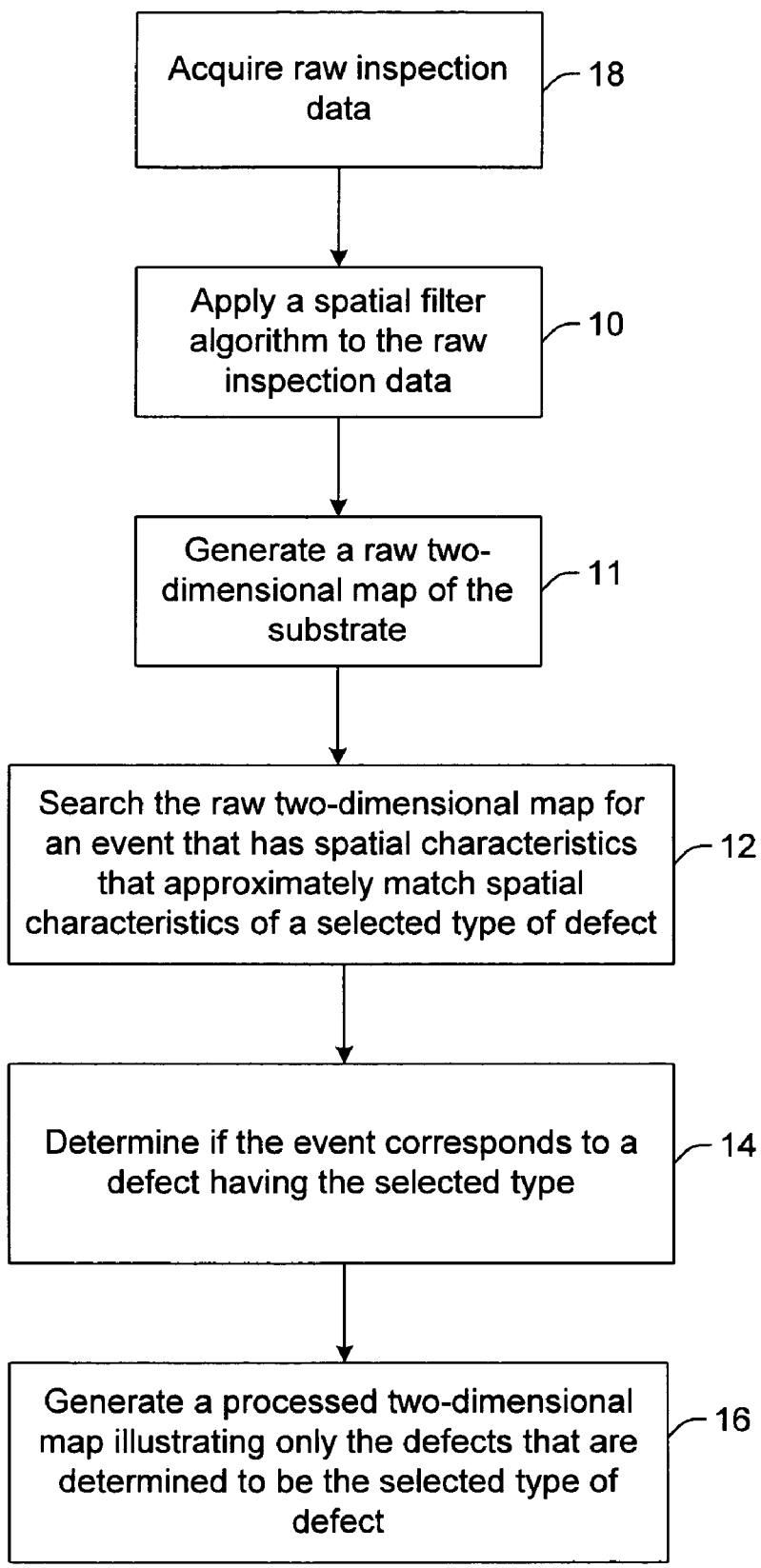
FIG. 1 is a flow chart illustrating one embodiment of a computer-implemented method for detecting defects on a substrate.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "substrate" is generally defined as a wafer or a reticle. As used herein, the term "wafer" generally refers to a substrate formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include only the substrate, which may be commonly referred to as a "virgin wafer." Alternatively, a wafer may include one or more layers formed upon a substrate. For example, such layers may include, but are not limited to, a resist, a dielectric material, and a conductive material. A resist may include any material that may be patterned by an optical lithography technique, an e-beam lithography technique, or an X-ray lithography technique. Examples of a dielectric material include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials such as "xerogels," and "high-k" dielectric materials such as tantalum pentoxide. In addition, examples of a conductive material include, but are not limited to, aluminum, polysilicon, and copper.

One or more layers formed on a wafer may be patterned or unpatterned. For example, a wafer may include a plurality of dies having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed. The term "semiconductor device" is used interchangeably herein with the term "integrated circuit." In addition, other devices such as microelectromechanical (MEMS) devices and the like may also be formed on a wafer.

A "reticle" or a "mask" is generally defined as a substantially transparent substrate having substantially opaque regions formed thereon and configured in a pattern. The substrate may include, for example, a glass material such as quartz. The substantially opaque regions may be formed of a material such as chromium. A reticle may be disposed above a resist-covered wafer during an exposure step of a lithography process such that the pattern on the reticle may be transferred to the resist. For example, substantially opaque regions of the reticle may protect underlying regions of the resist from exposure to an energy source. Many different types of reticles are known in the art, and the term reticle as used herein is intended to encompass all types of reticles.

As used herein, the term "raw inspection data" generally refers to data acquired by inspection of a substrate that has not been processed to alter the signal-to-noise ratio of the data. For example, raw inspection data may be data that has been translated from one form to another (e.g., digitized or transformed from one space to another). In addition, raw inspection data may be data that has been segmented into portions of raw inspection data, all of which has been acquired in one inspection of a substrate. However, the signal-to-noise ratio of the raw inspection data will be approximately equal to the signal-to-noise ratio of the inspection module that is used to acquire the data.

In some embodiments, the raw inspection data may include data that is acquired across an area of the substrate that equals approximately an entire area of a surface of the substrate. In other words, the raw inspection data may include inspection data acquired by a scan or an inspection of substantially an entire surface of the substrate. Therefore, unlike currently used defect detection methods that analyze inspection data on a point-by-point basis, the methods described herein detects defects by processing inspection data that spans a relatively large area on the surface of a substrate. In addition, unlike currently used defect detection methods, the methods described herein takes advantage of the shape of two-dimensional defects, when prescribed a priori, to recognize these defects among the total field of competing signals as described further herein.

Alternatively, the raw inspection data may include data that is acquired across a portion of a surface of the substrate. For example, an entire surface of a substrate may be scanned during inspection, and the inspection data may be segmented into portions, each or some of which may be used in the computer-implemented methods. Segmenting the data in such a manner may reduce the time in which processing of the data is completed, particularly if multiple segments are processed in parallel (e.g., using a parallel processor). In one example, the raw inspection data may be segmented into quadrants on the substrate. However, the raw inspection data may be segmented into any number of portions. The portions of the raw inspection data are preferably large enough so that the likelihood that an entire defect resides within one portion of the raw inspection data is relatively large. Therefore, the size of the portions that the raw inspection data is segmented into may vary depending on, for example, the lateral dimensions of the selected type of defect. In addition, the size of the portions of the raw inspection data will be substantially larger than an individual point in a scan of the substrate. Consequently, even if the raw inspection data is segmented, the detection methods and systems described herein will be unlike the currently used defect detection methods as described above.

The raw inspection data may also include data that is acquired by inspecting the front side of a substrate or the back side of a substrate. In the case of a wafer, the "front side" is defined as the surface of the wafer upon which devices will or can ultimately be formed. The "back side" is defined as the surface of the wafer upon which devices will not or cannot be fabricated.

The raw inspection data may contain a significant amount of noise. For example, the raw inspection data may have a relatively low signal-to-noise ratio. Usually, such raw inspection data cannot be used for defect detection since currently available methods for defect detection generally detect defects based solely on the signal strength at individual data points. For example, portions of relatively faint two-dimensional defects may be lost to background noise due to failure of its associated point defect signals to exceed a threshold. In some instances, noisy raw inspection data can be processed to improve the signal-to-noise ratio of the raw inspection data such that these detection methods can be used to detect defects with a greater degree of accuracy. However, such processing of the raw inspection data may only marginally improve the accuracy of these defect detection methods. In addition, such processing of the data may diminish or even remove portions of the inspection data that correspond to defects since the inspection data is relatively noisy.

In contrast, since the methods and systems described herein use the spatial characteristics of a selected type of defect to recognize these defects among the total field of competing signals, these methods and systems can extract very faint portions of the two-dimensional defect from a background of roughly 1.0 signal-to-noise ratio. Therefore, these methods can detect defects in relatively noisy raw inspection data with significant accuracy in addition to many other advantages over the currently used methods (e.g., elimination of processing of the raw inspection data for improving the signal-to-noise ratio, better accuracy with or without such processing, etc.).

Furthermore, the methods and systems described herein may be used to improve and extend the inspection capability of inspection hardware and configurations. For example, hardware architectures in wafer inspection tools, which generally include laser, optical path, and collector configurations, largely influence the relative signal of defects compared to overall field signal. Of course, distinctions in these architectures can afford considerable advantages for capturing a range of defect types over a range of sensitivities. However, as each architecture is pushed up against the technical limits of its designed performance, there becomes even greater value in methods that enable a given tool to better leverage its raw signal to generate more meaningful results. For example, raw inspection data, which is produced by an optical system that is optimized for particle defect detection but not scratches, may be processed as described herein to increase the accuracy with which scratches may be detected in the raw inspection data.

In some embodiments, the raw inspection data may include data that is acquired by optical inspection of the substrate. Optical inspection of a substrate may include scanning and imaging the substrate. Therefore, in one embodiment, the raw inspection data may include raw scan images of the substrate. Optical inspection data may be particularly useful in the methods and systems described herein since the optical inspection data can be acquired across a relatively large area of a substrate (e.g., an entire area of a substrate surface) in a relatively short amount of time. In addition, since the raw inspection data can contain a significant amount of noise without reducing the accuracy of the defect detection methods and systems described herein, the optical inspection data may be acquired using a number of different optical inspection systems, which may or may not be optimized for detection of the selected type of defect. The optical inspection systems that can be used with the methods and systems described herein include different types of optical systems such as reflectometers, scatterometers, ellipsometers, darkfield and/or brightfield optical subsystems, or some combination thereof. The optical inspection systems may also be non-imaging and/or imaging systems. In addition, the optical inspection systems may be single wavelength systems, spectroscopic systems, or some combination thereof.

However, it is to be understood that the methods and systems described herein may be used with any system that can generate inspection data across a two-dimensional space on a substrate. Examples of such systems include, but are not limited to, e-beam systems (e.g., scanning electron microscopes, etc.), scanning probe microscopes (e.g., atomic force microscopes, scanning tunneling microscopes, etc.), and x-ray systems (e.g., x-ray reflectometers, x-ray diffractometers, etc.).

As used herein, the term "non-point defect" generally refers to any defect that has some lateral extent in two-dimensions across a substrate, particularly across more than one measurement point on the substrate. In contrast, a "point defect" is generally defined as a defect that is detected at generally one measurement point on a substrate, and is therefore not considered to have any measurable lateral extent in two-dimensions across the substrate. It is to be noted that point defects can and are picked up in one or two adjacent data points, not because they are bigger than a data point but because scanning spots can be overlapped to help determine point defect location. This overlap is done not for understanding the spatial extent of the defect, but rather to help "triangulate" the defect positions (remember that these point defects are orders of magnitude smaller than our spot size). An extended defect is one that shows up in multiple scans (e.g., more than two) and each element of the extended defect can have a measured different xy location.

The term "selected type of defect" refers to a non-point defect. In one embodiment, the selected type of defect may be a scratch. The scratch may have an approximately linear shape. However, the scratch may have any other shape as well (e.g., nonlinear, circular, ellipsoidal, arcuate, etc.). Although the methods and systems described herein have proven to be particularly effective for detecting scratches, the methods and systems described herein may also be used to detect other types of non-point defects. For example, the selected type of defect may be a blob, a fiber, a chuck or handler pattern, or any other defect that has some lateral extent in two-dimensions. As used herein, the term "selected type of defect" also refers to any type of defect that is of interest to a user. In particular, the computer-implemented methods and systems described herein allow users, who are interested in finding specific, prescribed two-dimensional defects such as lines, arcs, circles, and rectangles, to extract those defects from raw inspection data such as wafer imaging data despite weak signal-to-noise signatures.

The type of defect that is selected for detection may also vary depending on the substrate and processes that have been performed on the substrate. For example, if the substrate is a wafer that has been polished (e.g., by chemical-mechanical polishing), then the selected type of defect may be a scratch. The particular shape of the scratch may also vary depending on the particular process that was used to polish the wafer. In another example, if the substrate is a wafer that has been cleaned (e.g., in a wet or dry cleaning process), then the selected type of defect may be a blob.

As used herein, the term "event" generally refers to a portion of a raw two-dimensional map that has a greater probability of corresponding to a selected type of defect than another portion of the raw two-dimensional map.

As used herein, the term "spatial characteristics" is generally defined as characteristics that define the two-dimensional extent of a non-point defect across a substrate. Therefore, the spatial characteristics define the two-dimensional shape of the non-point defect as well as the expected lateral dimensions of the non-point defect in the two dimensions. The spatial characteristics may be expressed using any form known in the art such as an equation, a function, an algorithm, a model, or some combination thereof.

Turning now to the drawings, FIG. 1 illustrates one embodiment of a computer-implemented method for detecting defects on a substrate. The computer-implemented method includes applying a spatial filter algorithm to the raw inspection data, as shown in step 10, to determine a first portion of the raw inspection data that has a higher probability of being a selected type of defect than a second portion of the raw inspection data. It is to be noted that the terms "first" and "second" are used herein only to distinguish between different portions of data and are not to be construed in any other manner. In one embodiment, applying the spatial filter algorithm may include extracting the first portion of the raw inspection data. In these embodiments, the spatial filter algorithm may also be used to determine two or more portions of the raw inspection data that have a higher probability of being a selected type of defect than other portions of the raw inspection data. In addition, the spatial filter algorithm may extract two or more portions of the raw inspection data that are more likely to be a selected type of defect than other portions of the raw inspection data.

In another embodiment, the computer-implemented method may include accentuating the first portion of the raw inspection data. Accentuating the first portion of the data may include altering a characteristic of the data points that make up the first portion of the raw inspection data. For example, the intensity or color of the data points that make up the first portion of the raw inspection data may be altered. In addition, if two or more portions of the raw inspection data are identified by the spatial filter algorithm, each of the two or more portions of the raw inspection data may be accentuated as described above. Each of the two or more portions of the raw inspection data may be accentuated to the same or different degrees and/or in the same or different ways. In addition, the degree to, and the manner in, which a portion of the raw inspection data is accentuated may vary depending on characteristics of the portion of the raw inspection data as well as characteristics of other portions of the raw inspection data.

In this manner, the first portion of the raw inspection data may be more easily distinguished from other portions of the raw inspection data in subsequent data processing. As such, the spatial filter algorithm can be used to better enhance the spatial features of the raw inspection data and to improve the signal-to-noise ratio. For example, in scratch detection, the line structures in the raw image data may be enhanced. This preprocessing stage provides a superior detection performance.

In the embodiments described above, the spatial filter algorithm can also specify the orientations of the defects that it will report. For example, the spatial filter algorithm may be set up to search for only scratch defects oriented in the vertical and horizontal directions. This feature can be very useful for slip line detection in wafer inspection.

The computer-implemented method also includes generating a raw two-dimensional map of the substrate, as shown in step 11. The raw two-dimensional map preferably illustrates the first portion of the raw inspection data identified in step 10. For example, the raw two-dimensional map may be generated using the data extracted in step 10. Therefore, the raw two-dimensional map may illustrate only the portion(s) of the data that have a higher probability of being a selected type of defect. Alternatively, the raw two-dimensional map may illustrate all of the raw inspection data including the portion(s) of the raw inspection data that were accentuated in step 10. In this manner, the two-dimensional map may have a relatively good signal-to-noise ratio. In another alternative, the raw two-dimensional map may illustrate only the accentuated portion(s) of the raw inspection data.

As shown in step 12, the method includes searching the raw two-dimensional map generated in step 11 for an event that has spatial characteristics that approximately match spatial characteristics of a selected type of defect. An event does not have to have spatial characteristics that exactly match the spatial characteristics of the selected type of defect. However, an event should have spatial characteristics that match the spatial characteristics of the selected type of defect within some margin of error. In this manner, searching the raw two-dimensional map identifies one or more events that have some likelihood of corresponding to the selected type of defect.

Searching the raw two-dimensional map for an event in step 12 may include, in one embodiment, applying a geometrical recognition algorithm to the raw two-dimensional map. Many geometrical recognition algorithms are known in the art, and selection of an appropriate geometrical recognition algorithm may vary depending on the spatial characteristics of the selected type of defect. For example, in one embodiment, the spatial characteristics of the selected type of defect may be substantially linear. In such an embodiment, a Hough transform may be applied to the raw two-dimensional map to search for events that have spatial characteristics that approximately match the spatial characteristics of the selected type of defect. For example, the Hough transform may be applied to the raw two-dimensional map to convert the data into a new space representation. This representation shows objects having a particular shape in point-like events that can then be thresholded as described below.

Further description of the Hough transform can be found in U.S. Pat. No. 3,069,654 to Hough, which is incorporated by reference as if fully set forth herein. In addition, the Hough transform that is used in this method may be a modified version of the Hough transform or a generalized Hough transform (GHT). For example, the Hough transform may be modified such that events having nonlinear spatial characteristics can be searched for in the raw two-dimensional map. Other examples of geometrical recognition algorithms that may be used in this method include the Sobel operator, the Prewitt operator, the Kirsch operator, and Robert's operator. Other appropriate algorithms may include a Fourier transform for periodic defects and a circle transform for circular shaped defects. In addition, a specialized transform or algorithm may be developed for a particular type of defect. For example, portions of one or more defect maps that are known to correspond to a particular type of defect may be used as templates to generate a transform or algorithm that can then be used to recognize geometrical two-dimensional shapes in raw two-dimensional maps. Furthermore, multiple transforms may be applied to the raw two-dimensional map separately or in combination.

The embodiment of the computer-implemented method shown in FIG. 1 also includes determining if the event corresponds to a defect having the selected type, as shown in step 14. In other words, this step involves taking events that have been identified as potentially corresponding to defects having the selected type and comparing them to some criteria to determine whether or not they actually correspond to the selected type of defect. In one embodiment, determining if the event corresponds to a selected type of defect includes applying a thresholding algorithm to the event. In addition, multiple thresholding algorithms may be applied to the event simultaneously or sequentially.

The thresholding algorithm can be derived in the transformed space and may be combined with one-dimensional defect information. For example, the thresholding algorithm may compare one or more characteristics of the events identified in step 12 to a predetermined threshold for each of the characteristic(s) in the transformed space. If the characteristic(s) of an event exceed the predetermined threshold(s), then the event may be determined to be a defect of the selected type. The characteristic(s) that are compared by the thresholding algorithm(s) may vary depending on the transformed space, the characteristic(s) of the selected type of defect and, in some instances, characteristics of the raw two-dimensional map. Thresholding algorithms are generally known in the art and, thus, will not be described further herein. In addition, thresholding algorithms may be modified depending on the characteristic(s) that are to be compared, and such modifications will be obvious to one of ordinary skill in the art. However, any appropriate algorithm or model known in the art may be used to determine if the event corresponds to a selected type of defect.

After thresholding the events and extracting those which are determined to correspond to the selected type of defect, the location of those events may be used to create a two-dimensional mask. The two-dimensional mask preferably has the same size as the raw two-dimensional map and is used to remove the non-selected types of defects from the raw two-dimensional map and to keep the selected type of defects. Therefore, the two-dimensional mask and the raw two-dimensional map may be used to generate a processed two-dimensional map of the substrate illustrating only the defects that are determined to be the selected type of defects, as shown in step 16. Since the processed two-dimensional map illustrates only the defects that have been determined to be the selected type of defect, the method can be used to produce maps that clearly illustrate only those defects which are of interest to the user. In addition, more than one two-dimensional map may be generated for one substrate. Each of the two-dimensional maps may illustrate different selected types of defects.

The processed two-dimensional map may be further processed, for example, by combining the processed two-dimensional map with other defect maps or other two-dimensional maps of the substrate, and/or generating other transformed maps of the substrate. The processing may also or alternatively include applying another thresholding algorithm to the raw inspection data and/or any other processing known in the art.

Although the embodiment of the computer-implemented method shown in FIG. 1 has been described with respect to one event, it is to be understood that searching the raw two-dimensional map may identify two or more events, each of which have spatial characteristics that approximately match the spatial characteristics of a selected type of defect. Therefore, the method may be used to detect multiple events on the substrate substantially simultaneously, each of which may correspond to the selected type of defect. The method may also include determining if each of (or at least some of) the two or more events correspond to the selected type of defect. Such determinations may be performed as described above. Determining whether or not each of (or at least some of) the multiple events correspond to the selected type of defect may be performed sequentially or substantially simultaneously.

Furthermore, although the embodiment of the computer-implemented method shown in FIG. 1 has been described with respect to one selected type of defect, it is to be understood that the method may be used to detect more than one selected type of defect sequentially or substantially simultaneously. For example, in one embodiment, the above-described computer-implemented method may be performed repeatedly, each time for a different type of defect. Alternatively, more than one selected type of defect may be detected substantially simultaneously. For example, the computer-implemented method may include, in some embodiments, substantially simultaneously searching the raw two-dimensional map for one or more events that have spatial characteristics that approximately match the spatial characteristics of more than one selected type of defect. In some embodiments, parallel processing may be used to search the raw two-dimensional map for events that match more than one selected type of defect at the same time.

Such an embodiment of the method may also include determining if the one or more events correspond to defects having one of the more than one selected type. In particular, this step involves determining only whether or not the event(s) correspond to the selected type of defect that their spatial characteristics approximately match. Determining whether or not each of (or at least some of) the multiple events correspond to a selected type of defect may be performed sequentially or substantially simultaneously. Determining whether or not each of the multiple events correspond to a selected type of defect may include applying a thresholding algorithm, another algorithm, or model to the events, as described further above. In addition, determining if the events correspond to each type of two-dimensional defect may be performed independently with different thresholding algorithms.

The embodiment of the computer-implemented method shown in FIG. 1 may also include one or more optional steps. For example, the computer-implemented method may, in some embodiments, include acquiring the raw inspection data, as shown in optional step 18. Acquiring the raw inspection data may include performing optical inspection of a substrate. The optical inspection may be performed using any of the optical systems described herein or any other optical inspection system known in the art. Examples of optical inspection systems that may be used to acquire the raw inspection data are the Surfscan SP1 based inspection systems and other optical inspection systems that are commercially from KLA-Tencor. Alternatively, acquiring the raw inspection data may include performing non-optical inspection of a substrate. For example, the raw inspection data may be acquired using one or more of the e-beam, scanning probe, or x-ray systems described herein and/or any other non-optical inspection system known in the art.

Acquiring the raw inspection data may include scanning an area on the substrate. In addition, acquiring the raw inspection data may include imaging an area on the substrate. Therefore, the raw inspection data may include raw scan images. For example, acquiring the raw inspection data may include detecting light reflected from an area on the substrate with a detector that has a two-dimensional photo-sensitive array (e.g., a charge-coupled device (CCD) camera or a time delay integration (TDI) camera) to form an image of the area. Such detectors are known in the art, and an appropriate detector may be selected based on the overall configuration of the optical inspection system.

Alternatively, acquiring the raw inspection data may include detecting light reflected from the substrate using a point detector such as a photomultiplier tube (PMT). Such detectors are known in the art. Therefore, the raw inspection data may include inspection data at individual points on the substrate, which are arranged into a two-dimensional format based on positional information about the individual points. The positional information about the individual points may be recorded during inspection as is known in the art. As a result, the raw inspection data may include a number of inspection data points that are acquired across an area on the substrate to which collectively a spatial filter algorithm may be applied as described above. Consequently, unlike the currently available methods in which individual data points are examined individually for the presence of a defect at each point, in the methods described herein, individual data points may be used as the raw inspection data, but a collection of individual data points are used in combination to detect the presence of a selected type of defect.

Figure 2:
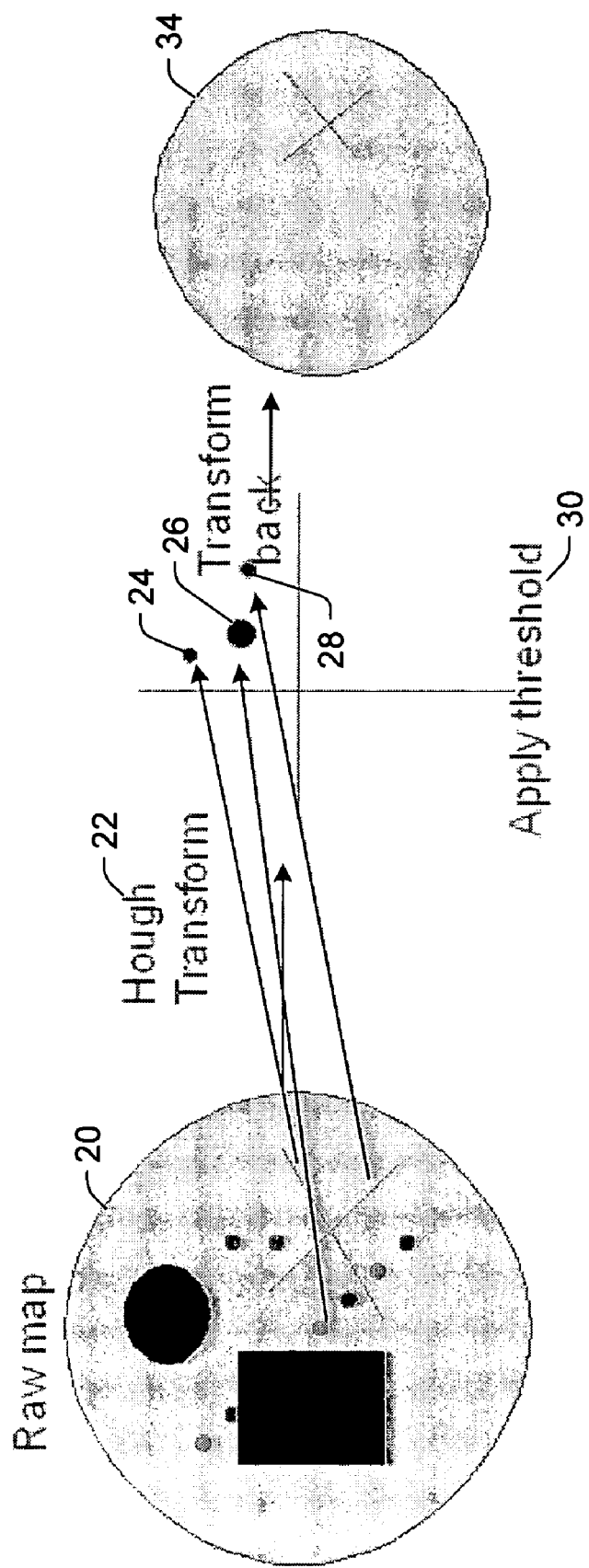
FIG. 2 is a conceptual diagram illustrating one example of defect detection results that can be generated using the computer-implemented method.

FIG. 2 is a conceptual diagram illustrating one example of defect detection results that can be generated using the computer-implemented method described above. In this example, the substrate is a wafer, and the surface that is inspected is the front side of the wafer. As shown in FIG. 2, raw two-dimensional map 20 can be generated as described above. For example, the raw two-dimensional map may be created from data extracted by the spatial filter algorithm or accentuated data (possibly in combination with non-accentuated data).

As shown in FIG. 2, Hough transform 22 is applied to the raw two-dimensional map to search for events that have spatial characteristics that approximately match spatial characteristics of a selected type of defect. In this example, the selected type of defect is a scratch having a substantially linear shape. The Hough transform converts the raw two-dimensional map into a new space representation. This representation shows linear shaped objects on the two-dimensional map in point-like events 24, 26, and 28. As shown in FIG. 2, events 24 and 28 correspond to scratches, but event 26 corresponds to a number of individual point defects that happen to fall in a line.

The computer-implemented method determines which of the events correspond to the selected type of defect by applying threshold 30 to events 24, 26, and 28. The threshold can be derived in the new space or combined with one-dimensional defect characteristics. For example, threshold 30 may compare one or more characteristics of the raw two-dimensional map corresponding to individual events to one or more characteristics of the selected type of defect. In this example, the threshold may compare the distance between individual point defects on the raw two-dimensional map that make up events 24, 26, and 28. If the individual point defects of an event are sufficiently close together, then the threshold may determine that the event corresponds to a scratch. In this manner, events 24 and 28 will be determined as events that correspond to a scratch, but since the individual point defects of event 26 are relatively far apart, as shown in the raw two-dimensional map, event 26 will be determined as an event that does not correspond to a scratch.

After thresholding the events and extracting those which are determined to correspond to the selected type of defect, the location of those events may be used to create a two-dimensional mask, which can be used to remove non-selected types of defects from the raw two-dimensional map thereby creating a processed two-dimensional map. As shown in FIG. 2, processed two-dimensional map 34 illustrates only the defects that are scratches. As such, processed two-dimensional map 34 provides a much simpler and clearer representation of the defects of interest than raw two-dimensional map 20.

Figure 3:
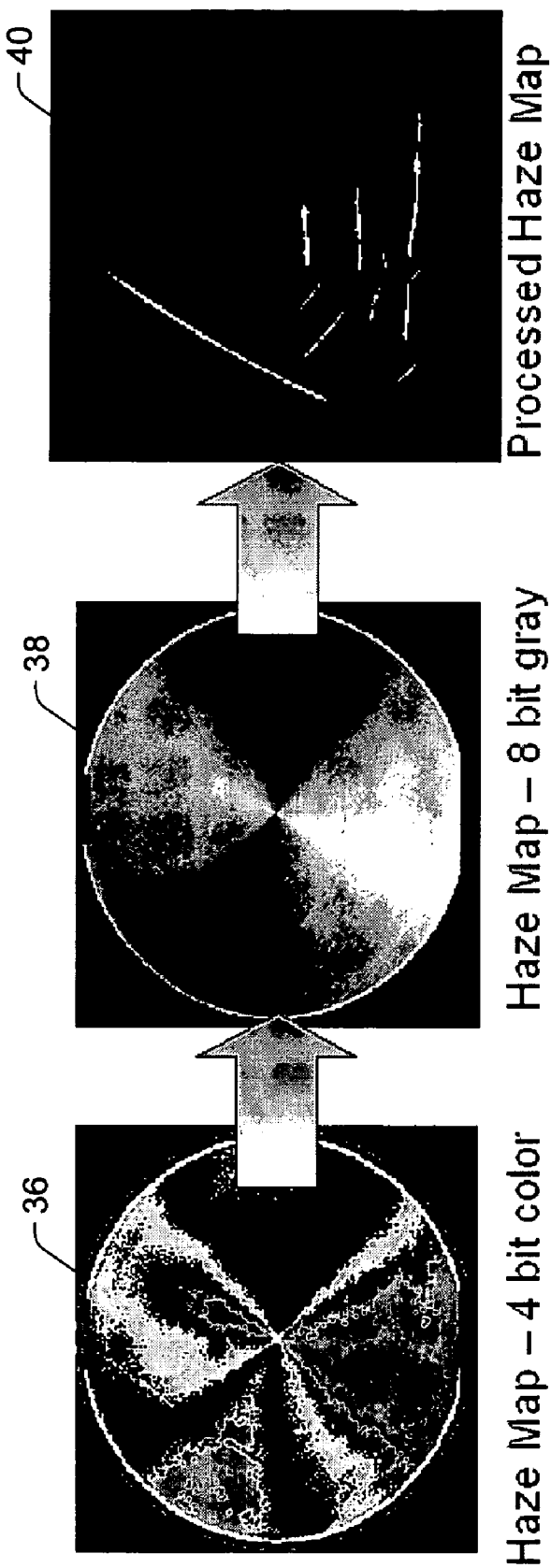
FIG. 3 illustrates one example of results that were generated after various steps of the computer-implemented method.

FIG. 3 illustrates one example of results that were generated after various steps of the computer-implemented method. These results are included herein only to illustrate the defect detection capability of the computer-implemented method, and are not to be construed as limiting embodiments. A front side of a wafer was scanned using an optical inspection system, and haze map 36 was generated in 4 bit color from the raw inspection data. As shown in haze map 36, the raw inspection data is relatively noisy.

A spatial filter algorithm was applied to haze map 36 to extract portions of the raw inspection data that have a higher probability of being a selected type of defect than other portions of the raw inspection data. In this example, a two-dimensional line filter was applied to the raw inspection data to extract portions of the raw inspection data from haze map 36 that may be the selected type of defect. Haze map 38 was generated in 8 bit gray to illustrate the extracted portions of the raw inspection data. As shown in FIG. 3, the portions of the extracted raw inspection data illustrated in haze map 38 are very faint (i.e., have relatively low intensity), and yet were extracted by the spatial filter algorithm.

Haze map 38 was then searched for events that have spatial characteristics that approximately match the spatial characteristics of the line defects. In this example, a Hough transform was applied to haze map 38 to identify those events that may correspond to line defects. A thresholding algorithm was then applied to the events identified by the application of the Hough transform to determine if the events correspond to line defects. The location of those events was used to create a two-dimensional mask, which has the same size as haze map 38. The two-dimensional mask was used to remove the particle-like defects from haze map 38 and to keep the line-like scratch defects thereby creating processed haze map 40. Therefore, as shown in FIG. 3, processed haze map 40 illustrates the line defects on the substrate in a much clearer manner than haze map 36 and haze map 38. In addition, as shown in processed haze map 40, although the raw inspection data contained a significant amount of noise, the computer-implemented method was able to detect several very faint line defects.

Figure 4:
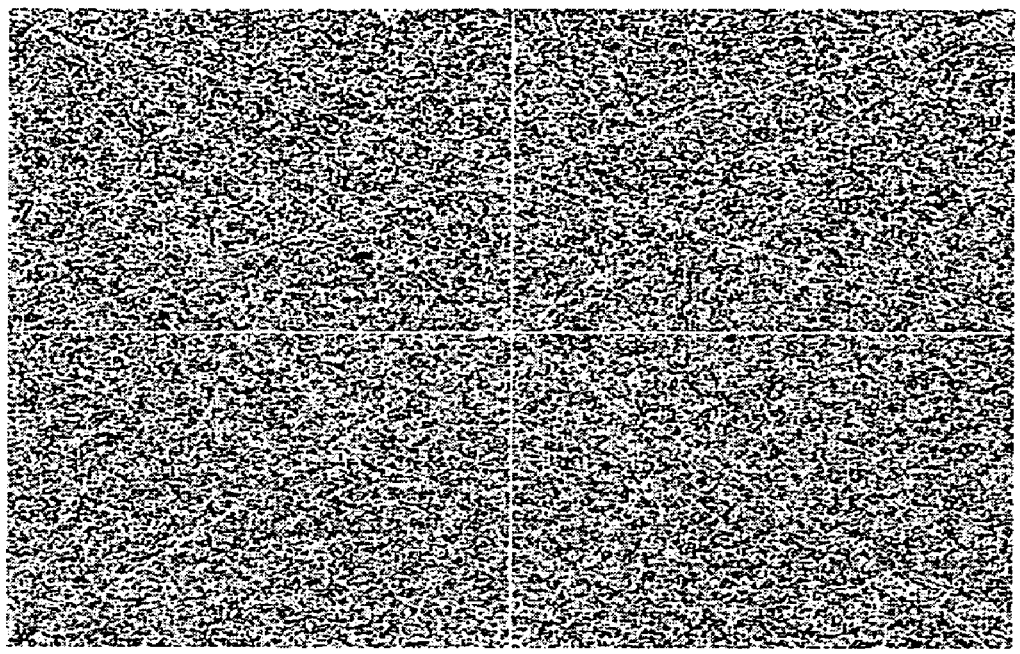
FIG. 4 illustrates one example of a two-dimensional map generated from raw inspection data.

Additional results that were generated after various steps of the computer-implemented method are also included herein only to illustrate the defect detection capability of the computer-implemented method, and are not to be construed as limiting embodiments. A front side of a wafer was scanned using an optical inspection system, and a two-dimensional map was generated from the raw inspection data. A portion of the two-dimensional map is shown in FIG. 4. As shown in FIG. 4, the two-dimensional map is relatively noisy.

A spatial filter algorithm was applied to the two-dimensional map to enhance portions of the raw inspection data that have a higher probability of being a selected type of defect than other portions of the raw inspection data. In this example, a two-dimensional line filter was applied to the raw inspection data to enhance portions of the raw inspection data from the two-dimensional map that may be the selected type of defect. The raw two-dimensional map shown in FIG. 5 was generated to illustrate the enhanced portions of the raw inspection data, as well as the non-enhanced portions of the raw inspection data. As shown in FIG. 4, the portions of the raw two-dimensional map that were enhanced are very faint (i.e., have relatively low intensity), and yet were identified by the spatial filter algorithm.

Figure 5:
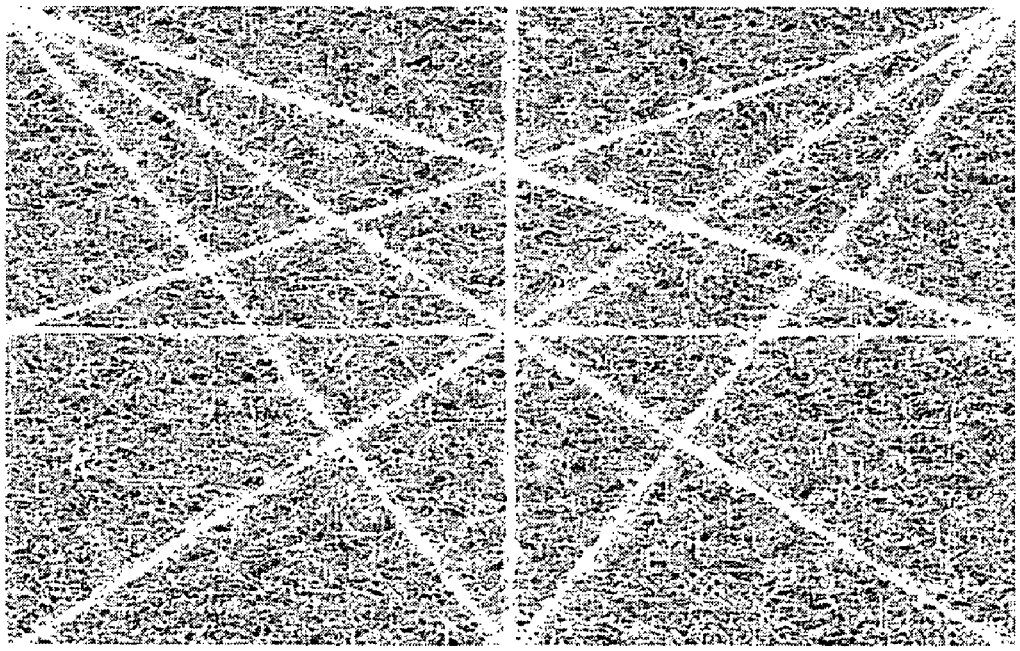
FIG. 5 illustrates one example of a raw two-dimensional map that was generated by processing the two-dimensional map of FIG. 4.

The raw two-dimensional map shown in FIG. 5 may then be searched for events that have spatial characteristics that approximately match the spatial characteristics of the line defects. For example, a Hough transform may be applied to the raw two-dimensional map to identify those events that may correspond to line defects. A thresholding algorithm may then be applied to the events identified by the Hough transform to determine if the events correspond to line defects. The location of those events may be used to create a two-dimensional mask, which has the same size as the raw two-dimensional map shown in FIG. 5. The two-dimensional mask may be used to remove the non-line defects from the raw two-dimensional map and to keep the line defects thereby creating a processed haze map. Therefore, the processed haze map may illustrate the line defects on the substrate in a much clearer manner than the two-dimensional maps shown in FIGS. 4 and 5.

Figure 6:
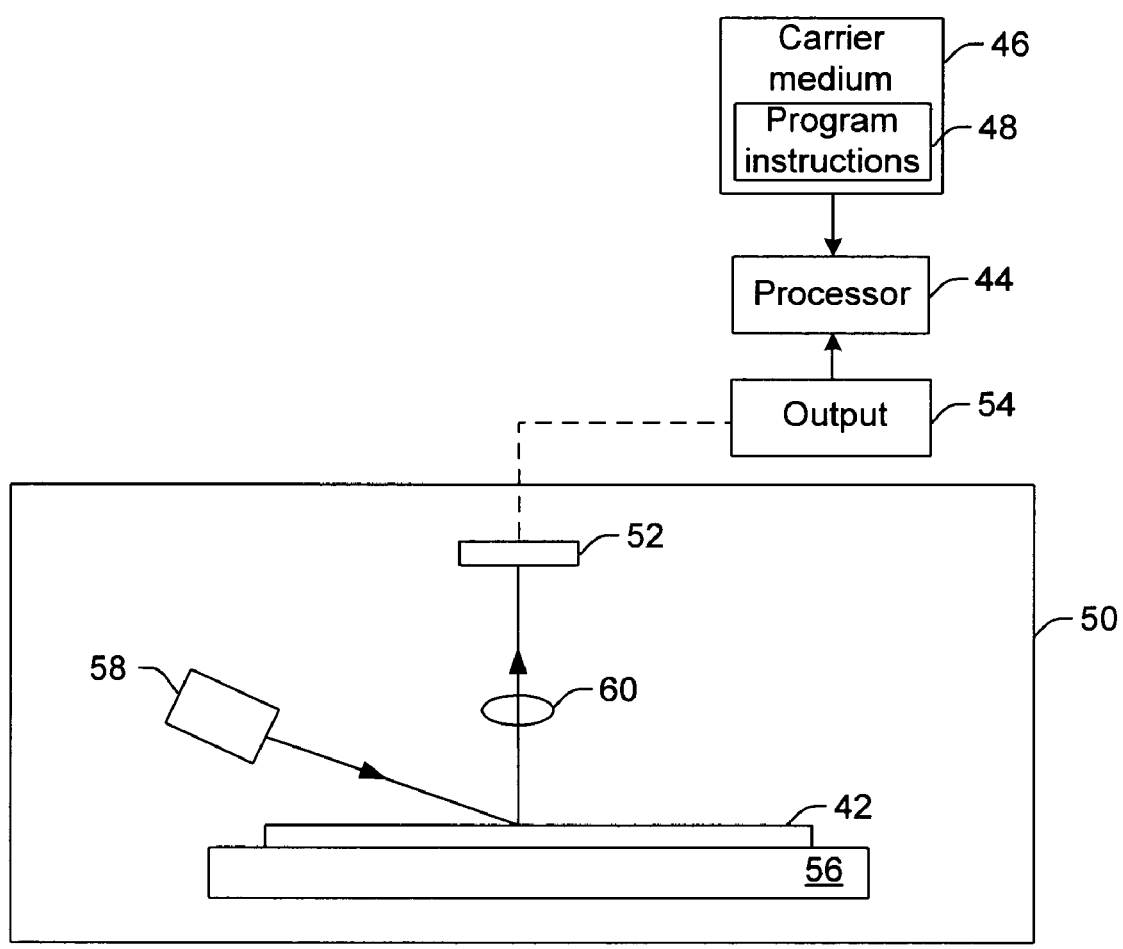
FIG. 6 is a schematic diagram illustrating one embodiment of a system configured to detect defects on a substrate.

Another embodiment relates to a carrier medium that includes program instructions executable on a processor. Examples of a carrier medium and program instructions are illustrated in FIG. 6, which is described further below. The program instructions are executable for applying a spatial filter algorithm to raw inspection data acquired across an area on a substrate to determine a first portion of the raw inspection data that has a higher probability of being a selected type of defect than a second portion of the raw inspection data. The program instructions are also executable for generating a raw two-dimensional map illustrating the first portion of the raw inspection data. Applying the spatial filter algorithm may be performed as described above. For example, applying the spatial filter algorithm may include extracting the first portion of the raw inspection data. In such an embodiment, the raw two-dimensional map may be generated such that it illustrates only the first portion of the raw inspection data. In another embodiment, the program instructions may be further executable for accentuating the first portion of the raw inspection data. In such an embodiment, the raw two-dimensional map may be generated such that it illustrates the accentuated portion of the raw inspection data. The second portion of the raw inspection data may or may not also be illustrated in such a raw two-dimensional map.

In addition, the program instructions are executable for searching the raw two-dimensional map for an event that has spatial characteristics that approximately match spatial characteristics of a selected type of defect. Searching the raw two-dimensional map may be performed as described above. For example, searching the two-dimensional map may include applying a Hough transform to the two-dimensional map. In such an embodiment, the spatial characteristics of the selected type of defect may be substantially linear.

The raw inspection data may include any of the raw inspection data described above. For example, the raw inspection data may contain a significant amount of noise. In another example, the raw inspection data may have a relatively low signal-to-noise ratio. In yet another example, the raw inspection data may include one or more raw scan images. In addition, the raw inspection data may include data acquired by optical inspection of the substrate. Furthermore, the area on the substrate, across which the raw inspection data has been acquired, may be equal to approximately an area of a surface of the substrate.

The selected type of defect may include any of the defects described above. For example, the selected type of defect may include a scratch in one embodiment. The substrate may include any of the substrates described above. For example, the substrate may include a semiconductor wafer, a patterned semiconductor wafer, or a reticle. The surface of the substrate may include any of those described above.

The program instructions are also executable for determining if the event corresponds to a defect having the selected type. Determining if the event corresponds to a defect having the selected type may be performed as described above. For example, determining if the event corresponds to a selected type of defect may include applying a thresholding algorithm to the event.

The program instructions may also be executable for performing any other steps of the computer-implemented method described above. For example, the program instructions may be executable for generating a processed two-dimensional map illustrating only the defect having the selected type. Generating a two-dimensional map may be performed as described above. In another embodiment, the program instructions may be further executable for substantially simultaneously searching the raw two-dimensional map for one or more events that have spatial characteristics that approximately match spatial characteristics of more than one selected type of defect. Such program instructions may also be further executable for determining if the one or more events correspond to defects having one of the more than one selected type. The carrier medium and the program instructions may be further configured as described herein.

Program instructions implementing methods such as those described herein may be transmitted over or stored on the carrier medium. The carrier medium may be a transmission medium such as a wire, cable, or wireless transmission link. The carrier medium may also be a storage medium such as a read-only memory, a random access memory, a magnetic or optical disk, or a magnetic tape.

In an embodiment, a processor may be configured to execute the program instructions to perform a computer-implemented method according to the above embodiments. The processor may take various forms, including a personal computer system, mainframe computer system, workstation, network appliance, Internet appliance, personal digital assistant ("PDA"), television system or other device. In general, the term "computer system" may be broadly defined to encompass any device having one or more processors, which executes instructions from a memory medium.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

FIG. 6 illustrates one embodiment of a system configured to detect defects on substrate 42. Substrate 42 may include any of the substrates described herein. The system includes processor 44. The processor may be configured as described above. In addition, the processor may include any suitable processor known in the art. For example, the processor may be an image computer or a parallel processor. The system also includes carrier medium 46. The carrier medium may be configured as described above. For example, carrier medium 46 includes program instructions 48, which are executable on processor 44. The program instructions may be executable for performing any of the embodiments of the computer-implemented method described above. The program instructions may be further configured as described above.

In some embodiments, the system may also include inspection module 50. Inspection module 50 may be coupled to processor 44. For example, one or more components of inspection module 50 may be coupled to processor 44 by a transmission medium (not shown). The transmission medium may include "wired" and "wireless" portions. In another example, detector 52 of inspection module 50 may be configured to generate output 54. The output may be transmitted across a transmission medium from detector 52 to processor 44. In some embodiments, the output may also be transmitted through one or more electronic components coupled between the detector and the processor. Output 54 may include raw inspection data generated by inspection module 50. The raw inspection data may include any of the raw inspection data described above. Therefore, output 54 is transmitted from the inspection module to the processor, and program instructions 48 may be executable on the processor to perform one or more of the computer-implemented methods described herein using output 54.

Inspection module 50 is shown in FIG. 6 as an optical inspection system that is configured to detect light scattered from a substrate. For example, the inspection module includes stage 56 upon which substrate 42 may be disposed during inspection. The stage may include any suitable mechanical or robotic assembly known in the art. The inspection module also includes light source 58. Light source 58 may include any appropriate light source known in the art. In this example, the light source is configured to direct light onto substrate 42 at an oblique angle of incidence. In addition, the inspection module includes collector 60, which is configured to collect light scattered from substrate 42 at angles that are approximately normal to an upper surface of substrate 42. The collector may include any suitable collector known in the art. As shown in FIG. 6, the collector may include a lens. However, the collector may alternatively include a combination of lenses or a reflective collector. The inspection module further includes detector 52, which is configured to detect light collected by collector 60. The detector is also configured to generate output 54, which includes the raw inspection data. The detector may include any of the detectors described above or any other suitable detector known in the art.

Although the inspection module is shown in FIG. 6 to inspect the substrate by detecting light scattered from the substrate, it is to be understood that the inspection module may have any other optical configuration known in the art. For example, the inspection module may be configured to inspect the substrate by detecting light reflected from the substrate. In addition, the inspection module may be configured as an ellipsometer, a reflectometer, a scatterometer, an interferometer, or some combination thereof. The inspection module may also be a non-imaging system, an imaging system, or some combination thereof. In addition, the inspection module may be a single wavelength system (e.g., a single wavelength ellipsometer), a spectroscopic system (e.g., a spectroscopic ellipsometer), or a combination thereof.

Furthermore, although the inspection module is shown in FIG. 6 as an optical inspection system, it is to be understood that the inspection module may be configured as a non-optical inspection system. For example, the inspection module may be configured as an e-beam system (e.g., a scanning electron microscope, etc.), a scanning probe microscope (e.g., an atomic force microscope, a scanning tunneling microscope, etc.), an x-ray system (e.g., an x-ray reflectometer, an x-ray diffractometer, etc.), any other non-optical inspection system known in the art, or some combination thereof. In addition, the inspection module may include a combination of one or more optical inspection systems and one or more non-optical inspection systems. For example, the inspection module may include an optical inspection system as well as an atomic force microscope.

Further modifications and alternative embodiments of various aspects of the invention may be apparent to those skilled in the art in view of this description. For example, methods and systems for detection of selected defects particularly in relatively noisy inspection data are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for detecting defects on a substrate, comprising:

applying a spatial filter algorithm to raw inspection data acquired across an area on the substrate to determine a first portion of the raw inspection data that has a higher probability of being a selected type of defect than a second portion of the raw inspection data, wherein the selected type of defect comprises a non-point defect;

generating a raw two-dimensional map illustrating the first portion of the raw inspection data;

searching the raw two-dimensional map for an event that has spatial characteristics that approximately match spatial characteristics of the selected type of defect; and determining if the event corresponds to a defect having the selected type.

2. The method of claim 1, wherein the raw inspection data contains a significant amount of noise.

3. The method of claim 1, wherein the raw inspection data has a relatively low signal-to-noise ratio.

4. The method of claim 1, wherein the raw inspection data comprises one or more raw scan images.

5. The method of claim 1, wherein the area on the substrate equals approximately an entire area of a surface of the substrate.

6. The method of claim 1, wherein the raw inspection data comprises data acquired by optical inspection of the substrate.

7. The method of claim 1, wherein the substrate comprises a wafer or a reticle.

8. The method of claim 1, wherein the substrate comprises a patterned wafer.

9. The method of claim 1, wherein the selected type of the defect comprises a scratch.

10. The method of claim 1, wherein said searching comprises applying a Hough transform to the raw two-dimensional map, and wherein the spatial characteristics of the selected type of defect are substantially linear.

11. The method of claim 1, wherein said determining comprises applying a thresholding algorithm to the event.

12. The method of claim 1, wherein said applying comprises extracting the first portion of the raw inspection data, and wherein the raw two-dimensional map illustrates only the first portion of the raw inspection data.

13. The method of claim 1, further comprising accentuating the first portion of the raw inspection data, wherein the raw two-dimensional map illustrates the accentuated first portion of the raw inspection data.

14. The method of claim 1, further comprising generating a processed two-dimensional map illustrating only the defect having the selected type.

15. The method of claim 1, further comprising substantially simultaneously searching the raw two-dimensional map for one or more events that have spatial characteristics that approximately match spatial characteristics of more than one selected type of defect and determining if the one or more events correspond to defects having one of the more than one selected type.

16. A storage medium, comprising program instructions executable on a processor for:

applying a spatial filter algorithm to raw inspection data acquired across an area on a substrate to determine a first portion of the raw inspection data that has a higher probability of being a selected type of defect than a second portion of the raw inspection data, wherein the selected type of defect comprises a non-point defect;

generating a raw two-dimensional map illustrating the first portion of the raw inspection data;

searching the raw two-dimensional map for an event that has spatial characteristics that approximately match spatial characteristics of the selected type of defect; and determining if the event corresponds to a defect having the selected type.

17. The storage medium of claim 16, wherein the raw inspection data contains a significant amount of noise.

18. The storage medium of claim 16, wherein the raw inspection data has a relatively low signal-to-noise ratio.

19. The storage medium of claim 16, wherein the selected type of the defect comprises a scratch.

20. The storage medium of claim 16, wherein said searching comprises applying a Hough transform to the raw two-dimensional map, and wherein the spatial characteristics of the selected type of defect are substantially linear.

21. The storage medium of claim 16, wherein said determining comprises applying a thresholding algorithm to the event.

22. The storage medium of claim 16, wherein said applying comprises extracting the first portion of the raw inspection data, and wherein the raw two-dimensional map illustrates only the first portion of the raw inspection data.

23. The storage medium of claim 16, wherein the program instructions are further executable for accentuating the first portion of the raw inspection data, and wherein the raw two-dimensional map illustrates the accentuated first portion of the raw inspection data.

24. A system configured to detect defects on a substrate comprising:

a processor; and a storage medium comprising program instructions executable on the processor for:

applying a spatial filter algorithm to raw inspection data acquired across an area on the substrate to determine a first portion of the raw inspection data that has a higher probability of being a selected type of defect than a second portion of the raw inspection data, wherein the selected type of defect comprises a non-point defect;

generating a raw two-dimensional map illustrating the first portion of the raw inspection data;

searching the raw two-dimensional map for an event that has spatial characteristics that approximately match spatial characteristics of the selected type of defect; and determining if the event corresponds to a defect having the selected type.

25. The system of claim 24, wherein the system further comprises an inspection module coupled to the processor, and wherein the inspection module is configured to generate the raw inspection data.

* * * * *